United States Patent [19]

Pearson

[11] 4,423,270
[45] Dec. 27, 1983

[54] PROCESS FOR CATALYTIC DEHYDRATION OF ETHANOL VAPOR TO ETHYLENE

[76] Inventor: Donald E. Pearson, 112 Clydelan Ct., Nashville, Tenn. 37205

[21] Appl. No.: 451,482

[22] Filed: Dec. 20, 1982

Related U.S. Application Data

[63] Continuation-in-part of Ser. No. 306,087, Sep. 28, 1981, abandoned.

[51] Int. Cl.$^3$ .............................................. C07C 1/00
[52] U.S. Cl. .................................................. 585/639
[58] Field of Search ........................................ 585/639

[56] References Cited

U.S. PATENT DOCUMENTS 2,220,430  11/1940  Stanley ................................ 585/639
2,569,092  9/1951  Deering ............................... 585/639
3,388,181  6/1968  Anspon ................................ 585/639

OTHER PUBLICATIONS

Pearson et al., *Ind. Eng. Chem. Prod. Res. Dev.*, 19, 245-250 (1980).

*Primary Examiner*—Curtis R. Davis

[57] ABSTRACT

Process for catalytic dehydration of ethanol vapor to ethylene is provided which is carried out in the presence of water vapor, the mixture of ethanol and water vapor being contacted with the catalyst bed containing a substituted phosphoric acid catalyst. The catalyst comprises a catalyst support having absorbed thereon a substituted phosphoric acid in which one of the hydroxyl groups thereof has been replaced by a hydrophobic organic group containing from 4 to 22 carbons.

10 Claims, No Drawings

PROCESS FOR CATALYTIC DEHYDRATION OF ETHANOL VAPOR TO ETHYLENE

RELATED APPLICATION

This application is a continuation-in-part of co-pending application Ser. No. 306,087, filed Sept. 28, 1981, and now abandoned.

BACKGROUND AND PRIOR ART

In recent years there has been increasing interest in ethanol, especially aqueous ethanol, as a feed stock for producing ethylene by catalytic dehydration. The basic dehydration reation is well known, and a number of different dehydration catalysts have been proposed and used for this purpose. Commercially, it appears that the preferred catalysts have been alumina or alumina-silica, such as alumina and magnesia deposited on a porous silica carrier. (See Haggin, C & EN, May 18, 1981, pages 52–54.) Bauxite activated with phosphoric acid ($H_3PO_4$) has been proposed. Chem. Abst., 91, 12305 (1979). A catalyst called Syndol, is stated to be used in the commercial production of ethylene from ethanol (N. K. Kochar, R. Merims, and A. S. Padia, Chem. Eng. Progr., June, 1981, 77, 66–70). The structure of the catalyst is not divulged however. Ethylene from this source contains about 2% of mixed hydrocarbons as impurities. Recently, experiments have been reported using polyphosphoric acid for the liquid phase conversion of ethanol to ethylene, the reaction being conducted on a batch basis with the polyphosphoric acid dissolved in the ethanol starting material. Pearson et al, Ind. Eng. Chem. Prod. Res. Dev., 19, 245–250 (1980).

During the unpublished experimental work leading to the present invention, polyphosphoric acid was applied to a porous granular support (viz. charcoal) and used as a vapor phase catalyst for the conversion of aqueous ethanol to ethylene. The catalyst was initially effective, but its conversion efficiency declined with increasing runs. It was determined that the polyphosphoric acid was being removed from the catalyst granules by the action of the water vapor (steam) present in the catalyst bed, water vapor being present in the aqueous ethanol feed stock and also being formed in the dehydration reaction. The use of phosphoric acid on a catalyst support is subject to this same defect, that is, it will be progressively removed from the granules of the catalyst bed where the vapor phase reaction is being carried out in the presence of large amounts of water vapor. The present invention provides a means for markedly reducing catalyst loss, and provides the art with a new and highly effective catalyst for the vapor phase dehydration of ethanol to ethylene as well as for other purposes in which water vapor is present in the catalyst bed.

SUMMARY OF INVENTION

The active ingredients of the catalysts used in the process of this invention are substituted phosphoric acids in which one or more of the hydroxyl groups has been replaced by a hydrophobic organic group. For example, the active catalysts may comprise benzenephosphonic acid, octadecanephosphonic aicd, or didecylphosphinic acid. The catalyst is absorbed on a porous granular catalyst support such as porous granules of carbon or charcoal. Because of the hydrophobic groups of the catalyst, its adherence to the catalyst support in the presence of water vapor is greatly improved, and the useful life of the catalyst is therefore remarkably extended. The catalyst is employed for the conversion of ethanol to ethylene in the presence of water vapor. The process has the advantage of suppressing the formation of oligomers (dimers, trimers, etc.), resulting in a high yield of ethylene.

DETAILED DESCRIPTION

The substituted phosphoric acid catalyst used in the process of this invention comprise a granular porous catalyst support compatible with phosphoric acid having absorbed thereon a catalytically effective amount of a substituted phosphoric acid in which at least one of the hydroxyl groups thereof has been replaced by a hydrophobic organic group containing from 4 to 22 carbons. The general formula of the preferred monosubstituted phosphoric acids is:

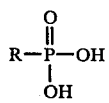

wherein R represents the hydrophobic organic group, which may be alkyl, aromatic or cyclic. In general hydrocarbon groups are preferred, such as those containing from 6 to 14 carbons. Specific examples of such groups include phenyl, biphenyl, cyclohexyl, octyl, decyl, octadecyl, etc. In other embodiments, two hydroxyl groups may be replaced by such hydrophobic groups. For example, the substituted phosphoric acid may be $(C_{10}H_{21})_2PO(OH)$, or other dialkyl or diarylphosphinic acids having the general formula:

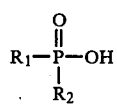

where $R_1$ and $R_2$ are alkyl or aryl groups of the kind described above. The di-substituted phosphinic acids are not as good catalytic dehydrating agents by themselves as the monoalkyl or the monoarylphosphonic acids.

The catalyst support may comprise any granular porous material which is compatible with phosphoric acid and which is stable under the conditions of use of the catalyst. A particularly preferred carrier for the catalyst is carbon or charcoal granules which are porous and provide a high surface area. For example, coconut charcoal granules are desirable. Compressed rods of carbon of 4–5 mm length and 1–2 mm diameter can also be used. Other catalyst supports which can be used include zeolites, silicates, silica gel, bauxite or alumina, and the like. The carrier itself may have catalytic activity, such as for dehydration of alcohols. The substituted phosphoric acid may be applied to the catalyst support in a volatile organic solvent solution. For example, benzenephosphonic acid or decanephosphonic acid may be dissolved in methanol, such as a 20 to 25% (w/v) solution and applied to the support granules, such as granular charcoal. The granules may be stirred on a batch basis with the solution of the substituted phosphoric acid, and the residual methanol evaporated to leave the substituted phosphoric acid in concentrated form on the granules.

After the catalyst has been prepared, it can be employed for catalytic reaction in either fixed or fluidized beds. In general, the catalyst beds are preferably employed for vapor phase reactions in which substantial amounts of water vapors are present, as in the conversion of aqueous ethanol to ethylene by vapor phase dehydration. That reaction runs most efficiently at temperatures in the range of about 300° to 400° C. For the catalysts of this invention, the feed stock need not be anhydrous ethanol, but feed stocks comprising 70 to 90% ethanol can be employed. The water vapor introduced with the feed stock and the water formed in the dehydration reaction even at the high temperatures involved are prevented from washing off the phosphoric acid because of the presence of the hydrophobic groups. At the same time, conversion efficiencies in the range of 95 to 100% can readily be obtained. The formation of oligomers or other by-products is suppressed.

In certain applications, where it is desired to reduce the cost of preparing the catalyst, catalysts of this invention can be employed together with an auxiliary phosphoric acid catalyst, such as phosphoric acid itself, or polyphosphoric acid. In preparing the catalyst, a mixture of the substituted phosphoric acid of this invention together with phosphoric acid or polyphosphoric acid will be applied to the catalyst support. The auxiliary catalyst will be gradually removed as the catalyst is used in the presence of water vapor, but it can be replaced by contacting the catalyst with a solution of phosphoric acid or polyphosphoric acid. In other words, the substituted phosphoric acid will remain on the support, while the auxiliary catalyst will comprise a replaceable component of the catalyst.

The catalysts of this invention and their application to the vapor phase dehydration of ethanol to ethylene are further illustrated by the following specific examples.

EXAMPLE 1

Benzenephosphoric acid, 52 g, was dissolved in 100 ml of methyl alcohol. This solution was poured on to 500 ml, 256 g, of coconut charcoal while the charcoal was stirred to obtain good distribution of the solution on all particles. Heat from a heat gun was directed on the surface of the charcoal while the latter was stirred until the particle appeared dry. The impregnated charcoal, containing 16.8% benzenephosphoric acid, was held in an oven at 125° C. overnight. It was then used to fill a 3 ft×1.25 in glass column which was connected to a condenser followed by a wet test meter. A typical run was made with a mixture of 100 ml of 95% ethyl alcohol and 15 ml of water giving an 80% ethanol-water solution as follows:

Ethanol, 80%, 1265 ml had already passed over catalyst. Now, 115 ml of 80% ethanol was added.

| Time | Temp (°C.) | Drops of alcohol/min | ml of ethylene/min |
|---|---|---|---|
| 1:30 | 354 | 49 | 222 |
| 2:25 | | 44 | 227 |
| 3:30 | | 41 | 204 |
| 5:15 | 340 | All in | |

| | |
|---|---|
| Final wet test meter | 36.8 l. |
| Theoretical | 36.5 l. |
| % | Quantitative |
| Water collected | 49 ml, dens. = 1.00 |
| Theor. | 48.3 ml |
| % | Quantitative |
| Total acid in water | 0.02 g calculated as benzenephosphoric acid |

EXAMPLE 2

The catalyst was prepared in a mixed acid form: 6.9% polyphosphoric acid and 7.16% benzenephosphoric acid on activated carbon. The results for a typical run are summarized below.

Double Alcohol (200 ml ethanol, 30 ml of water)

| Time | Temp (°C.) | Drops/min | Ml/min. | Total Gas |
|---|---|---|---|---|
| 7:50 PM | 390 | 58 | 168 | 0.05 T |
| 8:30 | 378 | 34 | 156 | 6.1 T |
| 10:00 | 320 | 86 | 666 | 47.5 |
| 11 PM | Run complete | | | 66.1 |
| 10 AM | | | | 72.75 |

99% Yield of ethylene
92% Yield of water, slight onion smell
Acid in water: 0.014 g of acetic acid; 0.18 g of $H_3PO_4$

EXAMPLE 3

Another mixed catalyst was prepared: 9.5% polyphosphoric acid and 1.1% didecylphosphinic acid [$(C_{10}H_{21})_2PO(OH)$; mp. 86°–87° C.; C, H, and P analysis within 0.2% for each element]. Results for a typical run were as follows.

| Time | Temp (°C.) | Drops/min | Ml/min | Total Gas |
|---|---|---|---|---|
| 10:40 | 420 | 68 | 233 | 6.2 l |
| 11:10 | 420 | 63 | 277 | 9.6 l |
| 11:40 | 420 | 64 | 312 | 17.3 l |
| 12:00 | 410 | 61 | 312 | 24.0 l |
| 12.35 | Run complete | | | |
| 8 AM | | | | 36.4 l |

Yield of ethylene 100%
Yield of water 94.6%
Acid in water 0.0066 g of acetic acid; 0.0991 g of $H_3PO_4$
Purity of ethylene: Typical analysis by G.C.
Capillary column: ethylene 98.74%, retention time = 2.22 min., ethyl alcohol 0.47%, retention time =
2.5 min; ether 0.03%, retention time
3.0 min (DP-13-78); no higher hydrocarbons.

EXAMPLE 4

Dimethyl n-octadecanephosphonate, 24 g, was impregnated on 400 ml of activated carbon, 6–10 mesh, in the manner previously described to give 11% catalyst on carbon. As soon as ester was heated in column, octadecanephosphoric acid was formed. The results of a double run are summarized below.

| Time | Drops/min | Ml/min | Total Gas |
|---|---|---|---|
| 9:00 | 60 | 333.3 | 3.1 l |
| 10:00 | 60 | 312 | 8.1 |
| 1 PM | 68 | 322 | 24. |
| 2 PM | Half in | | 29.5 |
| 3:10 | 20 | 50 | 38.3 |
| 3:45 | 33 | 100 | 40.7 |
| 11:05 | None. | Then to 91 dr/min | 42.1 |
| 8:30 AM | All in | | 70.1 |

Yield of ethylene 96%
Yield of Run 3 92%
Yield of water = 99%, density = 1.0
Acidity of collected water: 0.25 g of above acid, or less if acetic acid.

EXAMPLE 5

Benzylphosphoric acid, was impregnated on coconut charcoal, 6-14 mesh, in the manner previously described to give 14% acid on the charcoal. Results of a typical run are set out below.

| Time | Temp (°C.) | Drops/min | Ml/min | Total Gas |
|------|------------|-----------|--------|-----------|
| 8:15 | 360 | 103 | 666 | 11.1 l |
| 8:45 | 350 | 87 | 322 | 21.0 |
| 9:00 | 350 | 87 | 322 | 24.2 |
| 9:15 | All in | | | |
| 3 PM | | | | 32.3 l |

Yield of ethylene 88%
Yield of water 97%. Water had less odor than that from polyphosphoric acid Acidity. 0.0006 g of acetic acid; 1.02 g of benzylphosphoric acid.

EXAMPLE 6

The catalyst from Example 3 showed a reduced yield of ethylene after 17 runs (e.g. about 86%). Twenty one grams of 85% polyphosphoric acid was added dropwise to catalyst for regeneration while it was in reaction tube at 400° C. After addition, the tube was held at this temperature for several hours with nitrogen passing through. Further runs were made of which the following is representative.

| Time | Temp (°C.) | Drops/min | Ml/min | Total Gas |
|------|------------|-----------|--------|-----------|
| 3:55 | 420 | 96 | 400 | 2.2 l |
| 5:15 | 390 | 92 | 164 | 19.2 |
| 7:15 | 390 | 96 | 182 | 46.1 |
| 12:30 | 340 | 116 | 500 | 73.1 |
| 12:35 | Alcohol all added | | | 73.2 |
| 3 PM | | | | 74.0 |

Yield of ethylene 101%
Yield of water 99%
Acidity 0.01 g of phosphoric acid

EXAMPLE 7

The process and procedure of Example 1 can be repeated using as the mono-substituted phosphoric acid catalyst, biphenylphosphoric acid, instead of benzenephosphoric acid, and good results obtained.

What is claimed is:

1. In a process for the catalytic dehydration of an aqueous ethanol vapor to ethylene, the process improvement comprising carrying out said reaction in a catalyst bed containing a substituted phosphoric acid catalyst, said catalyst comprising a granular porous catalyst support compatible with phosphoric acid having absorbed thereon a catalytically effective amount of a substituted phosphoric acid in which at least one of the hydroxyl groups thereof has been replaced by a hydrophobic organic group containing from 4 to 22 carbons.

2. The process improvement of claim 1 in which said granular porous catalyst support is formed from carbon.

3. The process improvement of claim 1 in which said phosphoric acid is mono-substituted and contains a hydrophobic group having from 6 to 14 carbons.

4. The process improvement of claim 2 in which said granular porous catalyst support is formed from carbon.

5. The process improvement of claim 1 in which said substituted phosphoric acid is selected from the class consisting of octadecanephosphonic acid, benzenephosphonic acid, and biphenylphosphonic acid.

6. The improvement of claim 2 in which said substituted phosphoric acid is selected from the class consisting of octadecanephosphonic acid, benzenephosphonic acid, and biphenylphosphonic acid.

7. In a process for the catalytic dehydration of an aqueous ethanol vapor to ethylene, the process improvement comprising carrying out said reaction in a catalyst bed containing a substituted phosphoric acid catalyst, said catalyst comprising a granular porous catalyst support compatible with phosphoric acid having absorbed thereon a catalytically effective amount of a substituted phosphoric acid in which at least one of the hydroxyl groups thereof have been replaced by a hydrophobic organic group containing from 6 to 14 carbons and said substituted phosphoric acid is on said catalyst support in admixture with polyphosphonic acid.

8. The process improvement of claim 7 in which said granular porous catalyst support is formed from carbon.

9. The process improvement of claim 7 in which said phosphoric acid is mono-substituted and contains a hydrophobic group selected from the class consisting of octadecyl, phenyl, and biphenyl.

10. The process improvement of claim 8 in which said phosphoric acid is mono-substituted and contains a hydrophobic group selected from the class consisting of octadecyl, phenyl, and diphenyl.

* * * * *